United States Patent [19]

Wright et al.

[11] Patent Number: 4,513,104

[45] Date of Patent: * Apr. 23, 1985

[54] PROCESS USING IRON-THALLIUM CATALYSTS IN CO HYDROGENATION

[75] Inventors: Franklin J. Wright, Watchung; Michael A. Richard, Fanwood; James C. Pirkle, Lebanon, all of N.J.

[73] Assignee: Exxon Research and Engineering Co., Florham Park, N.J.

[ * ] Notice: The portion of the term of this patent subsequent to Mar. 12, 2002 has been disclaimed.

[21] Appl. No.: 478,915

[22] Filed: Mar. 25, 1983

Related U.S. Application Data

[63] Continuation-in-part of Ser. No. 299,014, Sep. 3, 1981, abandoned.

[51] Int. Cl.$^3$ ................................................ C07C 1/04
[52] U.S. Cl. .................................... 518/714; 518/717; 518/719; 518/720; 518/721
[58] Field of Search ............... 518/714, 717, 719, 721, 518/720

[56] References Cited

U.S. PATENT DOCUMENTS

| | | |
|---|---|---|
| 1,562,480 | 11/1925 | Wietzel et al. . |
| 2,711,420 | 6/1955 | Brown et al. . |
| 2,727,055 | 12/1955 | Seelig et al. . |
| 2,768,961 | 10/1956 | Weck et al. . |
| 2,815,357 | 12/1957 | Seelig et al. . |

FOREIGN PATENT DOCUMENTS

| | | |
|---|---|---|
| 635950 | 6/1927 | France . |
| 300294 | 11/1928 | United Kingdom . |
| 866161 | 11/1956 | United Kingdom . |

OTHER PUBLICATIONS

U.S. Bureau of Mines Report No. 5456 (1959).

*Primary Examiner*—Howard T. Mars
*Attorney, Agent, or Firm*—Robert J. North; Edward H. Mazer

[57] ABSTRACT

CO hydrogenation process is described utilizing novel thallium-promoted iron catalysts. Mixtures of $CO/H_2$ are selectively converted to liquid $C_6$-$C_{11}$ hydrocarbons containing $C_6$-$C_{11}$ aromatics, alpha-olefins and very small amounts of $C_{23}+$ hydrocarbon waxes.

22 Claims, No Drawings

PROCESS USING IRON-THALLIUM CATALYSTS IN CO HYDROGENATION

CROSS REFERENCE TO RELATED APPLICATIONS

This application is a continuation-in-part application of U.S. Ser. No. 299,014, filed Sept. 3, 1981 abandoned.

BACKGROUND OF THE INVENTION

The Fischer-Tropsch process is one of several processes involving the hydrogenation of carbon monoxide and is well-known for producing hydrocarbons and hydrocarbon fuels by contacting mixtures of carbon-monoxide/hydrogen, with generally an iron-based catalyst. The produced hydrocarbons usually contain a broad range of liquid paraffins and olefins of $C_5$-$C_{20}$ carbon number, and under conditions of excess hydrogen, an especially valuable portion being the linear and branched paraffinic $C_6$-$C_{11}$ fraction, the well-known "gasoline" fraction useful for internal combustion engines.

An extensive amount of work has been carried out in an effort to modify and improve the selectivity of the process in producing the gasoline fraction directly under efficient process conditions, having improved octane number. Particular process conditions which are highly desirable to achieve these goals are high percent CO conversion, low methane make, high liquid hydrocarbon make containing aromatics and olefins in the $C_5$-$C_{11}$ hydrocarbon fraction and a low wax make (i.e., $C_{23+}$ hydrocarbons).

A commercially practiced Fischer-Tropsch process uses mixtures of carbon monoxide/hydrogen that are contacted with a potassium-doped iron catalyst, as a fluid bed, at about 320° C. to 330° C. under pressure. However, a significant quantity of wax formation occurs, and further, the resulting liquid hydrocarbons generally only comprise about 5 weight percent aromatics.

What is desired in the art is a process which is more selective in producing $C_6$-$C_{11}$ liquid hydrocarbons and in producing aromatics and olefins particularly in the $C_6$-$C_{11}$ liquid hydrocarbon portion. Particularly desired is where the process can be conducted under very efficient conditions of high percent CO conversion, high liquid hydrocarbon make, containing $C_6$-$C_{11}$ aromatics and/or alpha olefins, low methane make and low $C_{23+}$ hydrocarbon wax make.

SUMMARY OF THE INVENTION

It has been found that a composition comprising a mixture of iron compounds and thallium compounds is an efficient catalyst in a CO hydrogenation process for selectively promoting the production of $C_6$-$C_{11}$ liquid hydrocarbons, containing $C_6$-$C_{11}$ aromatic hydrocarbons and/or alpha olefins at high percent CO conversion with attendant low methane and wax production.

The catalyst composition contains compounds of iron and thallium in an iron-thallium weight ratio of 100:1 to 1:100, respectively, taken as the free metals, and the composition can be supported or unsupported and contain catalyst promoter agents and additives as well. In a preferred embodiment, the iron value in the composition is initially substantially in the trivalent state. To achieve high selectivity to hydrocarbons, and preferably $C_6$-$C_{11}$ liquid hydrocarbons and $C_6$-$C_{11}$ aromatics, it is necessary to pretreat the catalyst to convert the initially trivalent iron substantially to reduced and carbided iron. The initially trivalent and/or monovalent thallium is reduced to zero valent thallium during this pretreatment. Thus, the preferred catalyst, in its working state, consists of reduced and carbided iron promoted by metallic thallium. It has been found by thermal analysis techniques, that the monovalent and/or trivalent thallium is reduced to metallic thallium first during pretreatment and that metallic thallium promotes the subsequent reduction of oxidized iron to metallic iron and iron carbide.

The hydrocarbons produced in the process comprise gaseous $C_1$-$C_4$ hydrocarbons and $C_5$-$C_{23}$ liquid hydrocarbons, including linear and branched paraffins and olefins, together with small amounts of oxygenates such as methyl alcohol or ethyl alcohol. The amount of $C_{23+}$ hydrocarbon waxes is generally about 5 weight percent or less and preferably less than about one weight percent. The ratio of paraffins/olefins produced in the process can be regulated by the hydrogen partial pressure, i.e., increasing the $H_2$ partial pressure increases paraffins/olefins ratio. In addition, in the process, alpha olefins are obtained in good yield in the temperature range of about 270° to 350° C., and aromatics in the $C_6$-$C_{11}$ liquid fraction are obtained in good yield at temperatures above 350° C. The $C_6$-$C_{11}$ liquid hydrocarbons produced usually comprise about 40 weight percent and above of the total hydrocarbons produced, and of the liquid hydrocarbons produced, about 65 weight percent and greater is comprised of $C_6$-$C_{11}$ hydrocarbons. The gasoline fraction, the $C_6$-$C_{11}$ fraction, generally contains about 5 weight percent or greater of aromatic $C_6$-$C_{11}$ hydrocarbons. However, depending upon the particular process conditions used, higher or lower amounts of the above-stated hydrocarbon products may be formed.

In accordance with this invention, there is provided a process for producing liquid hydrocarbons, including those in the $C_6$-$C_{11}$ hydrocarbon range, comprising the steps of:

(a) first contacting a supported or unsupported catalyst composition comprising a mixture of iron compounds and thallium compounds, wherein the weight ratio of iron-thallium, taken as the free metals, is from about 100:1 to 1:100, and wherein said iron compounds contain iron value substantially in the trivalent state, by contacting said catalyst with a mixture of CO and $H_2$ in a volume ratio of about 1:4 to 4:1, respectively, at a temperature ranging from 270° to 550° C., a pressure ranging from 0.1 to 10 MPa and a space velocity ranging from 10 to 10,000 v/v/hr., or equivalent conditions, to substantially convert said thallium compounds to metallic thallium and said iron compounds to reduced and carbided iron; and (b) continuing said contacting as described in step (a) at a pressure above 0.1 MPa to produce liquid hydrocarbons comprising about 40 weight percent and greater $C_6$-$C_{11}$ liquid hydrocarbons and below about 5 weight percent $C_{23+}$ hydrocarbons.

DESCRIPTION OF THE INVENTION AND PREFERRED EMBODIMENTS

The catalyst composition in the process is capable of selectively producing $C_6$-$C_{11}$ liquid hydrocarbons from carbon monoxide and hydrogen under efficient process conditions. The $C_6$-$C_{11}$ hydrocarbon fraction contains a significant percentage of $C_6$-$C_{11}$ aromatic hydrocarbons, produced at process temperatures above 350° C., which are extremely effective as octane-increasing agents for motor gasoline, and alpha olefins, produced at process temperatures from 270° to 350° C. being useful chemicals in the chemical industry. Further, use of the catalyst under Fischer-Tropsch conditions results in a surprisingly low $C_{23+}$ hydrocarbon wax make. The reason why the combination of iron-thallium compounds in a mixture is unique in producing these very desirable results is not at all clear. One theory that we do not wish to be bound by is that iron and thallium form a redox couple that is selective in forming aromatics and other hydrocarbons under the process conditions.

The performance of thallium promoted iron catalysts is similar in some respects to conventional commercial potassium promoted CO hydrogenation catalysts. However, thallium promoted iron catalysts provide the following advantages over potassium promoted iron catalysts: no need for sintering or other high temperature treatment during catalyst preparation (K promoted catalyst preparation usually requires sintering at temperatures above about 500° C. to achieve intimate Fe-K contact in the catalyst mixture); no significant wax formed (K promoted iron produces several percent wax); and very high activity, especially at lower space velocities and higher temperatures.

The catalyst composition consists essentially of a mixture of iron compounds and thallium compounds, wherein the weight ratio of iron-thallium, taken as the free metals, is about 100:1 to 1:100, in which the iron value is regarded as being initially substantially in the trivalent state. This is based on the fact that use of ferric compounds in the composition and use of an oxidizing atmosphere, e.g. air, in the drying step during preparation of the compounds leads to desired results. By the term "consisting essentially of", as used herein, is meant that other materials, known in the art as being promoters, activators, supports and catalytic-aiding materials, may also be present, as long as the unique capability of the subject catalyst in producing $C_6-C_{11}$ liquid hydrocarbons in the absence of significant amounts of $C_{23+}$ hydrocarbon waxes, is not adversely effected. By the term "mixture of iron compounds and thallium compounds" is meant a physical admixture, solid solution, alloy, spinel, or new compound formed from the compounds in which the compounds can be simply combined, co-precipitated, precipitated individually, and then combined or formed by impregnating one solid compound with a solution of another to produce the composition.

A thorough description of the catalyst composition is described in a related application, U.S. Ser. No. 418,380, filed 9-15-82, hereby incorporated by reference, which describes catalyst components and weight ratios, additives, promoter agents and the like, and methods of preparation.

The weight ratio of iron-thallium, taken as the free metals and referred to herein as Fe/Tl, being in parts by weight in the composition is from 100:1 to 1:100, preferably from 100:1 to 35:65, particularly preferred from about 100:1 to 65:35 and most preferred from about 100:10 to 80:20, respectively.

The catalyst composition contains iron initially substantially in its trivalent state in order to convert CO and $H_2$ to $C_6-C_{11}$ aromatic and other hydrocarbons, and by the term "substantially" is meant at least about two-thirds of the iron present, such as in the case of $Fe_3O_4$.

It is to be understood that an iron-based catalyst which is subjected to oxidizing conditions prior to CO hydrogenation, such that a significant amount of ferric ion is formed on the catalyst surface, is also regarded as being an operable embodiment and included within the scope of the subject catalyst.

Iron compounds and thallium compounds operable in the composition are inorganic or organometallic and include their oxides, hydroxides, carbides, nitrates, carbonates, halides, sulfates, and the like, and mixtures thereof. Representative examples include $Fe_2O_3$, $Fe_3O_4$, $Fe(OH)_3$, $Fe_5C_2$, $Fe(NO_3)_3$, $Fe_2(CO_3)_3$, $FeCl_3$, $Fe(NH_4)(SO_4)_2$, $Tl_2O$, $TlNO_3$, $Tl_2CO_3$, $Tl_2SO_4$, $TlCl_3$, $TlCl$, $TlF$ and the like, preferred compounds are iron oxide, thallium oxide, thallium chloride, thallium fluoride, thallium nitrate, or mixtures thereof. Also preferred are where said iron compounds contain iron value substantially in the trivalent state, and for purposes of this application, since the true valence of iron in iron carbides is not exactly known, but can be assumed to be at least partially in an oxidized state, iron carbides are intended to be included within the class of iron compounds wherein the iron is substantially in the trivalent state. Also operable are organometallic compounds of iron or thallium which decompose to the respective oxides under the process conditions, e.g., thallium acetate and iron oxalate. Preferably the thallium value is substantially impregnated on the surface of the catalyst composition.

Particularly preferred compounds are the oxides of the two metals which can be formed, for example, by precipitating the metal values from aqueous solution of their soluble nitrates or sulfates by the addition of a base to form the respective hydrated oxides, which are dried and heated in the presence of air and converted to the metallic oxides. Thus, a preferred composition is a mixture of iron oxide and thallium oxide.

The subject catalyst composition can be supported or unsupported and is preferably supported. This preference is because the supported catalyst has, in general, a longer catalyst lifetime and a lesser tendency to disintegrate during continued operation. Representative examples of supports include alumina, alkali-doped alumina, silica, titanium dioxide, magnesium oxide, magnesium carbonate, magnesium silicate, silicon carbide, zirconia, Kieselguhr, talc, clay, and the like. By the term "alkali-doped alumina", as used herein, is meant a mixture of alumina and about 1 to 20 mole percent of an alkali metal salt, based on the moles of alumina, such as potassium carbonate, potassium silicate, cesium carbonate and the like. Mixtures of supports can also be utilized, including those above, for example, alumina and magnesium oxide. Preferred supports for the catalyst in the process for producing $C_6-C_{11}$ aromatic hydrocarbons include cesium-doped alumina, or alumina, magnesium oxide, or mixtures thereof.

The amount of said support present can be from about 50 to 99 weight percent, based on the combined weight of said iron/thallium compounds, said support preferably being 75 to 95 weight percent of the total weight of catalyst composition.

Various additives and promoter agents can also be utilized with the catalyst, including cobalt, zinc, magnesium, barium, nickel, chromium, manganese, and compounds or salts thereof, such as cobalt oxide, zinc oxide, chromium oxide and the like, which increases the activity and selectivity of the catalyst and thus reduces the required temperature in the process. Also operable are alkali metal salts, such as potassium salts, e.g., potassium carbonate, potassium oxide, potassium bicarbonate, potassium hydroxide, rubidium carbonate, alkali metal borates and silicates; other metals, such as zirconium, cerium, vanadium, rare earth elements, tantalum and molybenum; and halide salts, e.g., fluoride salts such as ammonium fluoride, potassium fluoride and the like, also for promoting the formation of liquid hydrocarbons. In addition, other additives/promoters can be used including, but not limited to, alumina, manganese oxide, magnesium oxide, thorium oxide, calcium oxide, titanium dioxide and the like, to help maintain the stability and integrity of the catalyst. Preferred promoters for the catalyst are cobalt, zinc, magnesium, as their salts or oxides, ammonium fluoride, potassium carbonate, or mixtures thereof.

Amounts of promoters or additives that can be used in the compositions are from about 1 to 200 weight percent, based on the weight of iron, taken as the free metals.

For example, cesium, as the carbonate salt, is generally used in about 1 to 25 weight percent, cesium taken as the metal, to dope an alumina carrier. Ammonium fluoride is used in about a 0.1 to 10 weight percent, based on the weight of iron as the free metal, as a promoter, and potassium carbonate is used in about a 0.1 to 5 weight percent, based on the weight of iron, as the free metal, to promote the subject composition. Cobalt and zinc, as their salts or oxides, are generally used in about a 1 to 20 weight percent, based on the weight of iron, as the free metal, to promote the catalyst.

Representative examples of catalyst compositions are (giving the composition and the weight ratio of the metals or elements in the free state) $Fe_2O_3/Tl_2O_3$ (10:1 Fe/Tl); $Fe_2O_3/Tl_2O_3/NH_4F$ (100:10:2 Fe/Tl/F); $Fe_2O_3/Tl_2O_3/K_2CO_3$ (100:10:1 Fe/Tl/K); $Fe_3O_4/Tl_2O_3$ (10:1 Fe/Tl); $Fe_2O_3/TlNO_3$ (10:1 Fe/Tl); $Fe_2O_3/CoO/TlNO_3$ (100:52.3:10 Fe/Co/Tl); and $Fe_2O_3/ZnO/TlNO_3$ (100:53.2:10 Fe/Zn/Tl).

A preferred catalyst composition is an iron oxide/thallium oxide on cesium-doped alumina, wherein cesium is present, as the metal, in about 13 weight percent of the alumina; iron, as the free metal, is present in about 10 weight percent of the combined weight of the cesium-doped alumina; and thallium is present, as the metal, in about 10 to 20 weight percent of iron.

The catalyst composition can be made by a variety of techniques. The simplest method is to mix together an iron compound and a thallium compound, which are finely ground, in the proper ratio, and utilize the catalyst as is.

Another method is to co-precipitate the iron and thallium metal values from aqueous solution by the addition of base to precipitate the hydrated metal oxides. The resulting mixture is collected, washed and dried in air to yield the mixture of the corresponding oxides. The drying step is preferably carried out in air, and preferably under the influence of heat.

To insure a highly active catalyst, it is preferable to remove any excess alkali salts that might be initially present on the surface of the iron hydroxide. Also, iron exchange agents such as soluble ammonium compounds, can be used to wash the precipitated iron hydroxide. Alternatively, an ammonium salt, such as ammonium bicarbonate, can be used to precipitate the metal hydroxide from the solution.

A still further method of preparing the catalyst compositions is to precipitate one metal value from an aqueous solution of its salt by the addition of base, or adjustment of the pH of the solution, and to isolate the metal oxide thereof. The same procedure is then used for the other metal value and the two resulting metal oxides are mixed together to form the subject catalyst.

A particularly preferred method for making the iron-thallium catalysts is via the "incipient wetness" impregnation technique whereby a known amount of thallium salt, such as thallium nitrate, is dissolved in distilled water and added dropwise with thorough stirring to finely divided, solid water-insoluble iron compounds to insure even dispersion on the solid surface by the thallium salt. Uniform distribution is insured by adding only just enough thallium solution to wet the entire surface of the iron solid to take advantage of the surface spreading forces.

A further method for making the catalyst composition in which at least one preferably finely divided, solid iron-containing compound is contacted with a concentrated aqueous solution of at least one soluble thallium compound, preferably the nitrate, thereby substantially impregnating the surface of the iron compound, and then drying said impregnated iron-containing compound in the presence of an oxidizing atmosphere, preferably air, thereby resulting in said composition, wherein said iron value is substantially in the trivalent state. Particularly preferred is where the thallium compound is substantially impregnated on the surface of the catalyst composition. The resulting solid can be air-dried at room temperature, vacuum-dried at elevated temperature, or preferably heat-dried in air, and then ground into a fine particle size and used as is in the process.

The obtained catalyst compositions, including that prepared by the subject method, generally has a surface area from about 5 to 300 $m^2/gm$. After the required pretreatment in the process with, preferably, a mixture of CO and $H_2$, the catalyst surface size reduces to about 1 to 50 $m^2/gm$.

The subject matter of the instant invention is a process for producing liquid hydrocarbons in the $C_6$-$C_{11}$ hydrocarbon range comprising $C_6$-$C_{11}$ aromatic hydrocarbons and alpha olefins, and below about 5 weight percent $C_{23+}$ hydrocarbon waxes.

The process is conducted by contacting a mixture of CO and $H_2$ with a supported or unsupported catalyst composition that has been pretreated and comprising a mixture of iron compounds and thallium compounds wherein the ratio of iron-thallium, taken as the free metals, is from about 100:1 to 1:100. A thorough description of operable iron-thallium catalysts useful in the process is given hereinabove for the subject composition including weight ratios, different iron and thallium compounds operable, additives, promoter agents and the like, and methods of preparation. The scope of iron-thallium catalysts operable in the subject process is broader than for the subject composition in that it is intended to include all mixtures comprising iron-thallium compound combinations which result in the production of $C_6$-$C_{11}$ liquid hydrocarbons containing $C_6$-$C_{11}$ aromatic hydrocarbons and alpha olefins, and less than about 5 weight percent $C_{23+}$ hydrocarbon waxes. Thus, the iron-thallium based catalyst useful in the process also comprises the use of other co-catalysts, and supports, not specifically described herein, and combinations in which the iron value may not be substantially in the trivalent state or where the thallium value may not be substantially impregnated on the catalyst surface. Preferred embodiments of iron-thallium combinations are described hereinabove in the discussion of the catalyst.

By the term "mixtures of CO and $H_2$" is meant mixtures of pure CO and $H_2$, or impure mixtures, also containing water, $CO_2$ and the like, and including "water gas", "synthesis gas", "Town gas" and the like. A preferred mixture is that produced by gasification apparatus, such as a Shell-Koppers Gasifier.

The ratio of CO and $H_2$ as $CO/H_2$, in the process is about 4:1 to 1:4, preferably 2:1 to 1:2, and particularly preferred about 1:1, respectively.

A volume ratio of 2:1 $CO/H_2$ can be produced by commercial coal gasifiers, and an excess of CO in the feedstream also tends to reduce the amount of light gases produced in the process.

The temperature of the process, after catalyst pretreatment, is conducted at about 230° to 550° C., preferably about 270° to 400° C. The temperature range between 270° to 350° C. favors alpha olefin formation and from 350° to 550° C., $C_6$-$C_{11}$ aromatics are produced in significant quantity.

The pressure of the $CO/H_2$ feedstream in the process is above about 0.1 MPa to about 10 MPa (1 to 100 atmospheres) and preferably about 0.5 to 1.5 MPa and particularly preferred, about 0.8 MPa.

The space velocity of the $CO/H_2$ feedstream is maintained at about 10 to 10,000 v/v/hr., preferably about 100 to 2500 v/v/hr. and particularly preferred of about 150 to 1500 v/v/hr.

A particularly preferred embodiment of the subject process comprises contacting a mixture of CO and $H_2$, in about a 1:1 volume ratio, respectively, with a supported catalyst composition, which has been pretreated, comprising a mixture of iron oxide and thallium nitrate or oxide, the weight ratio of iron-thallium, taken as the free metals, in the composition, being from about 100:1 to 35:65. The iron oxide of the catalyst composition contains iron value, substantially in the trivalent state, and thallium compound is substantially impregnated on the surface of the iron catalyst composition, which is supported on aluminum oxide, magnesium oxide, or mixtures thereof. The catalyst is pretreated in a mixture of CO and $H_2$ at elevated temperature to convert the catalyst to its working form, wherein said working catalyst consists of thallium metal and reduced and carbided iron.

The pretreatment procedure comprises heating the mixture of thallium compounds and substantially trivalent iron in a mixture of CO and $H_2$ in about 4:1 to 1:4, and preferably a 1:1 volume ratio, respectively, to a temperature of 270° to 550° C. and preferably at about 270° C., at 0.1 to 10 MPa and preferably 0.1 MPa total pressure, and a space velocity of about 10 to 10,000 v/v/hr, preferably 300 to 500 v/v/hr, for a sufficient time to result in a reduced and carbided iron catalyst.

The hydrogen synthesis process is preferably conducted at a temperature of about 270° to 400° C., a pressure of about 0.5 to 1.5 MPa, and a space velocity of about 150 to 1500 v/v/hr., producing liquid hydrocarbons in the $C_6$-$C_{11}$ range, comprised of $C_6$-$C_{11}$ aromatic hydrocarbons and alpha olefins and less than about one weight percent $C_{23}+$ hydrocarbon waxes. Particularly preferred embodiments are where: the product $C_6$-$C_{11}$ liquid hydrocarbons comprise at least about 10 weight percent $C_6$-$C_{11}$ aromatic hydrocarbons at temperatures above 350° C.; 20 weight percent alpha olefins at 270° to 350° C.; and at least 40 weight percent $C_6$-$C_{11}$ liquids at 270° to 400° C. process temperatures.

The apparatus which is used for the process can be any of the conventional types, wherein the catalyst is used in the form of a fixed bed, fluid bed, slurry and the like. Preferred is the catalyst in the form of a fixed or fluid bed.

The process is generally conducted by placing the composition catalyst into the reaction zone of the reactor and pretreating the catalyst prior to the run. The pretreatment step, as described hereinabove, can be conducted by passing a reducing gas, such as $H_2$, CO, or $NH_3$, or mixtures thereof, either simultaneously or sequentially over the catalyst at elevated temperature for a certain period of time, which is dependent upon the amount of catalyst used, type of reactor and the like. During this pretreatment step, the catalyst is contacted with a reducing atmosphere which converts the metal oxides to metal carbides, carbonitrides and the like, or the reduced metal, as shown by X-ray analysis. The exact composition of the catalyst during the actual run is not known and actually may be continuously changing in nature during the run. It is, however, believed that iron is in a reduced and/or carbided state substantially during the process. After the pretreatment step, the feedstream gases, comprising CO and $H_2$, are passed into the catalyst zone for reaction.

Methods of collecting and separating the obtained hydrocarbons are conventional and include, for example, atmospheric and reduced pressure distillation.

The following comparative examples and examples illustrate the subject matter which we regard as our invention, and the examples are illustrative of the best mode of carrying out the invention, as contemplated by us, and should not be construed as being limitations on the scope and spirit of the instant invention.

EXAMPLE 1

Preparation of the Catalyst 100 Fe:52.3 Co:10 Tl (Catalyst One)

Two thousand ml. of an aqueous solution of 404 g. of ferric nitrate and 145 g. cobalt nitrate, was heated to boiling; 1500 ml. of an aqueous solution of 316 g. ammonium bicarbonate was added thereto with stirring. The combined solutions were heated for about 15 minutes, whereupon a precipitate formed. The mixture was cooled, the solid filtered off and washed with distilled water until the washings were neutral. The solid was dried in a vacuum oven at 100° C. for 12 hours. It was removed and ground to a fine particle size. The solid was then impregnated by the technique of "incipient wetness" by dropwise addition of an aqueous solution of 7.3 g. thallium nitrate in 70 ml. water, whereupon all of the thallium nitrate solution was adsorbed by the dispersed solid. The resulting solid was dried in a vacuum oven a 110° C. for 12 hours to yield 123 g. of dark-colored solid. Analysis of the solid revealed that it consisted of 45.5 weight percent of iron, as the metal, and the iron, cobalt and thallium in a weight ratio of 100:52.3:10, each taken as the metal.

EXAMPLE 2

Preparation of the Catalyst 10:1 Fe/Tl (Catalyst Two)

To a boiling solution of 404 g. ferric nitrate nonahydrate in 1.5 liters of distilled water was added with stirring a solution of 237 g. ammonium bicarbonate dissolved in 1.5 liters water resulting in the precipitation of iron oxide. The resulting solution was kept boiling until all $CO_2$ evolution had ceased. The precipitate was filtered, washed with distilled water until the wash water was neutral. The washed solid was dried in a vacuum at 110° C. for 12 hours. The resulting solid was impregnated by the technique of incipient wetness by the dropwise addition to the solid of a solution of 7.3 g. thallium nitrate in 70 ml. of water. The ferric oxide adsorbed practically all of the solution. The impregnated solid was dried in a vacuum oven at 110° C. for 12 hours. The resulting impregnated solid weighed 86 g. an analyzed for 10 parts by weight iron, per 1 part thallium, taken as the free metals.

EXAMPLE 3

The following supported and unsupported iron-thallium catalysts were prepared as described below.

Catalyst Three (100 Fe:10 Tl, supported on Alumina)

A solution of ferric nitrate was deposited on an alumina support to yield $Fe_2O_3$-alumina having an iron loading of about 14 weight percent of the composition as metallic iron. The solid had an initial BET surface area of about 41 $m^2/g$. The solid was impregnated with thallium nitrate by the technique of incipient wetness using an aqueous solution of thallium nitrate. After drying overnight in a vacuum oven at 110° C., the solid had an Fe/Tl weight ratio of 100:10, taken as the free metals.

Catalyst Four (100 Fe:10 Tl, supported on Cs-doped alumina)

Beta aluminum trihydrate was impregnated with the required amount of cesium nitrate using the wellknown technique of incipient wetness to yield a solid containing 10 mole percent cesium, taken as the metal. The resultant solid was heated in an air oven at 870° C. for 8 hours and then mixed with ferric nitrate crystals, which had been heated until they melted and dissolved in their own water of crystallization (approximately 80°-85° C.). The resulting impregnated solid was then placed in an air oven at 110° C. for 12 hours, and under these conditions, decomposition of the nitrate to the oxide occurred yielding a solid containing 10 weight percent each of Fe and Cs, taken as the free metals. Then, by the incipient wetness technique, the solid was impregnated with thallium nitrate to yield a solid having a Fe/Tl weight ratio of 100:10.

Catalyst Five (100 Fe:10 Tl, unsupported)

This catalyst was prepared as described above for Catalyst Two, except that commercially available iron oxide, as opposed to precipitated iron oxide, as used for Catalyst Two, was impregnated with thallium nitrate solution by the technique of incipient wetness, wherein the weight ratio of Fe/Tl, taken as the free metals, was 100:10.

Catalyst Six (100 Fe:10 Tl:2F, unsupported)

This catalyst was prepared by adding an aqueous solution of ammonium fluoride, by the technique of incipient wetness, to Catalyst Five, described above. The resulting catalyst contained Fe/Tl/F, in a weight ratio, as the free elements, of 100:10:2.

Catalyst Seven (100 Fe:20 Tl, supported on $Al_2O_3$)

This catalyst was prepared by the procedure described above for Catalyst Two, except that the incipient wetness impregnation step was performed twice with aqueous thallium nitrate yielding a resulting solid having an Fe/Tl weight ratio of 100:20 taken as the free metals.

Catalyst Eight (100 Fe:20 Tl:2F, supported on $Al_2O_3$)

This catalyst was prepared by adding ammonium fluoride to the Catalyst Seven, described above, by the technique of incipient wetness resulting in a catalyst having the composition of 100 Fe:20 Tl:2F, by weight, taken as the free elements, on $Al_2O_3$.

Catalyst Nine (100 Fe:10 Tl, as the chloride)

This catalyst was prepared by impregnating iron oxide with aqueous thallium chloride by the technique of incipient wetness, as described above for Catalyst Five, except that thallium chloride was used instead of thallium nitrate, yielding a solid having an Fe/Tl weight ratio of 100:10, as the free metals.

Catalyst Ten (100 Fe:52.3 Zn:10 Tl)

An iron-zinc catalyst, 100 Fe:52.3 Zn:10 Tl, was prepared according to the general procedure of Example 1 except that zinc nitrate was used in place of cobalt nitrate.

Catalyst Eleven (2.5 Fe:1Tl, unsupported)

A catalyst was prepared according to the general procedure for Catalyst Two, except that the thallium nitrate loading was adjusted so that the final composition had an atomic ratio of Fe/Tl of 2.5/1, (corresponding to an Fe/Tl weight ratio of 100:150).

Catalyst Twelve (4Fe:1Tl, supported on MgO—$Al_2O_3$

A catalyst prepared consisted of iron promoted with thallium (Fe/Tl weight ratio 4:1) supported on a magnesium-alumina spinel. This supported catalyst contained 5 weight percent of iron. The catalyst was prepared by melting 90 g. of ferric nitrate at 80° C. in a large evaporating dish. To this liquid was added 4.0 g. of thallium nitrate and 250 g. of spinel support with constant stirring in order to insure uniform and total impregnation. The solid was placed in a vented oven maintained overnight at 200° C. at which temperature the nitrates was substantially decomposed to the respective oxides.

EXAMPLE 4

The catalysts prepared and described in Examples 1-3 were run under Fischer-Tropsch conditions at elevated temperatures and the runs all produced liquid hydrocarbons in the $C_6$-$C_{11}$ range, containing $C_6$-$C_{11}$ aromatics, $C_2$-$C_{15}$ alpha olefins and low amounts of $C_{23+}$ wax.

EXAMPLE 5

A 10:1 Fe/Tl catalyst was prepared by the incipient wetness technique, as described above in Example 2 and tested by the following procedure for Fischer-Tropsch synthesis.

The catalyst was tested in a fixed bed tubular reactor fitted with a highly conductive brass sleeve. Catalyst pretreatment consisted of flowing a mixture of $H_2/CO/N_2$ (49:50:1, by volume, approx.) over the catalyst at 270° C., 1 atm. pressure, and a space velocity of 500 v/v/hr. for 18 hours. The pressure was then raised to 120 psia. The pretreatment was continued for two more hours at which time the temperature was maintained at 270° C. or increased in the range of 270° to 375° C. The space velocity was adjusted in the range of 150 to 1200 v/v/hr. Liquid samples were collected at 4° C. and gas analyses were performed by in-line gas chromatography. A highly conductive brass sleeve was placed in the ¾ inch space between the surrounding furnace and the ½ inch O.D. stainless steel 5" long reactor tube. This presumably has two favorable effects: (1) it prevents natural convection of air which tends to lead to axial temperature gradients; and (2) it normalizes and dissipates temperature gradients created by heats of reaction. A traveling 1/16 inch thermocouple positioned in a ⅛ inch O.D. stainless steel tube at the reactor center indicated that the axial temperature gradients in the reactor were reduced to ~1° C./cm up to 300° C. and to ~2°-5° C./cm up to 350° C.

The performance of thallium-promoted iron under these conditions is shown in the following tables:

TABLE I

| | CO Conversion: | |
|---|---|---|
| Temp. | Space Velocity | CO Conversion |
| 270° | 150-1200 | 90-20% |
| 300° | 150-1200 | 65-40% |
| 325° | 150-1200 | 96-80% |
| 350° | 150-1200 | 97-90% |

TABLE II

| | Methane Selectivity: | |
|---|---|---|
| Temp. | Space Velocity | $CH_4$ (% of Total Hydrocarbon) |
| 270° | 150-1200 | 6-4% |
| 300° | 150-1200 | 6-3% |
| 325° | 150-1200 | 6-10% |
| 350° | 150-1200 | 9-15% |

TABLE III

| | Liquid ($C_5$-$C_{11}$) Selectivity: | |
|---|---|---|
| Temp. | Space Velocity | $C_5$-$C_{11}$ (% of Total HC) |
| 270° | 150-1200 | 50-54% |
| 300° | 150-1200 | 51-57% |
| 325° | 150-1200 | 50-51% |
| 350° | 150-1200 | 42-51% |

TABLE IV

| | Gas ($C_4^-$) Selectivity | |
|---|---|---|
| Temp. | Space Velocity | $C_4^-$ (% of Total HC) |
| 270° | 150-1200 | 35-30% |
| 300° | 150-1200 | 34-26% |
| 325° | 150-1200 | 35-39% |
| 350° | 150-1200 | 39-50% |

TABLE V

| | α-Olefin Selectivity in $C_6^+$ Fraction: | |
|---|---|---|
| Temp. | Space Velocity | $C_6^+$ α-Olefin (% of Total HC) |
| 270° | 150-1200 | 21-26% |
| 300° | 150-1200 | 23-26% |
| 325° | 150-1200 | 21-16% |
| 350° | 150-1200 | 14-8% |

TABLE VI

| | Aromatics Selectivity: | |
|---|---|---|
| Temp. | Space Velocity | Aromatics (% of Total HC) |
| 270° | 150-1200 | 2-3% |
| 300° | 150-1200 | 2-3% |
| 325° | 150-1200 | 4-8% |
| 350° | 150-1200 | 7-14% |

As is initially seen in the above data, Fe/Tl catalyst is an active Fischer-Tropsch catalyst for producing hydrocarbons.

Further, it was observed that under the process conditions used, there was a relatively weak dependence on the space velocity in the process with respect to methane selectivity, liquid $C_5$-$C_{11}$ selectivity, gaseous $C_1$-$C_4$ hydrocarbons, alpha-olefin and aromatic selectivity. However, a significant dependence of percent CO conversion on space velocity was observed particularly at lower temperatures.

EXAMPLE 6

Utilizing the general procedure described in Example 5, the following runs were made with a catalyst of the composition: 100 Fe:20 Tl; prepared as described in Example 2. Portions of the same catalyst batch were run under substantially the same conditions in three different reactors to determine possible apparatus effects in the data. Run No. 3 was conducted in the apparatus described in Example 5, and runs 1 and 2 were conducted in other fixed bed tubular reactors. The reactors used in Runs 1 and 2 were similar to the apparatus described in Example 5, except that the bed length used in Run 1 was about 36" long, and the bed length used in Run 2 was about 3" long. The three runs were conducted at 270° C., at a pressure of 0.9 MPa and a feedstream containing a $CO/H_2$ molar ratio of 1.0. Results are given below.

TABLE VII

| Comparison of 100 Fe:20 Tl Catalyst at 270° C. in Three Different Reactors; P = 0.9 MPa, Feed = 1.0 CO/1.0 $H_2$ | | | |
|---|---|---|---|
| Run | 1 | 2 | 3 |
| GHSV | 300 | 300 | 375 |
| Run Time (min.) | 1380 | 1311 | 1080 |
| % CO Conversion | 76 | 53 | 51 |
| Selectivity, wt. % of Hydrocarbons | | | |
| $CH_4$ | 5.2 | 7.4 | 6.7 |
| $C_2H_4$ | 4.8 | 6.4 | 3.2 |
| $C_2H_6$ | 1.4 | 2.0 | 3.3 |
| $C_3$ | 12.8 | 21.3 | 10.8 |
| $C_4$ | 16.8 | 17.4 | 10.4 |
| $C_5+$ | 59 | 43 | 65 |
| % Aromatics in | | | |
| $C_6$ | 1.1 | N.M.[a] | 1 |
| $C_7$ | 2.5 | 9 | 3.3 |
| $C_8$ | 6.5 | 6 | 9.1 |
| $C_9$ | 6.7 | | 12.9 |
| $C_{10}$ | | | 11.1 |
| $C_{11}$ | | | 2.7 |

[a]N.M. = Not Measured.

As is seen from the data there is general agreement in hydrocarbon selectivities. The small differences among the runs can be attributed to the slight variations in the reactor configurations and run conditions.

EXAMPLE 7

Utilizing the procedure and different sets of apparatus described in Example 6, the same catalyst was tested under the same conditions, but at 325° C. Results are given in the following table.

TABLE VIII

Comparison of 100 Fe:20 Tl Catalyst at 325° C. in Three Different Reactors; P = 0.9 MPa, Feed = 1.0 CO/1.0 $H_2$

| Run | 1 | 2 | 3 |
| --- | --- | --- | --- |
| GHSV | 300 | 300 | 200 |
| Run Time (min.) | 1320 | 1387 | 1080 |
| % CO Conversion | 97 | 95 | 97 |
| Selectivity, wt. % of Hydrocarbons | | | |
| $CH_4$ | 5.8 | 8.1 | 14.2 |
| $C_2H_4$ | 4.1 | 3.5 | 2.4 |
| $C_2H_6$ | 2.4 | 4.3 | 3.8 |
| $C_3$ | 12.5 | 18.9 | 11.0 |
| $C_4$ | 14.7 | 13.0 | 10.0 |
| $C_5+$ | 60 | 52 | 61 |
| % Aromatics in | | | |
| $C_6$ | 2.8 | 4 | 4.7 |
| $C_7$ | 8.2 | 17 | 11.2 |
| $C_8$ | 12.0 | 13 | 15.6 |
| $C_9$ | 13.0 | | 15.7 |
| $C_{10}$ | | | 13.6 |
| $C_{11}$ | | | 5.8 |

As is seen from the data, there is good general agreement in the hydrocarbon selectivities.

EXAMPLE 8

Example 6 was repeated utilizing the same catalyst, the same apparatus, and the same process variables, except that the temperature was raised to 350° C. Results are given below in the Table IX.

TABLE IX

Comparison of 100 Fe:20 Tl Catalyst at 350° C. in Three Different Reactors; P = 0.9 MPa, Feed = 1.0 CO/1.0 $H_2$

| Run | 1 | 2 | 3 |
| --- | --- | --- | --- |
| GHSV | 377 | 386 | 300 |
| Run Time (min.) | 1300 | 1170 | 1440 |
| % CO Conversion | 96 | 95 | 45 |
| Selectivity, wt. % of Hydrocarbons | | | |
| $CH_4$ | 7.2 | 9.6 | 16.6 |
| $C_2H_4$ | 4.7 | 4.4 | 1.3 |
| $C_2H_6$ | 2.4 | 3.3 | 4.2 |
| $C_3$ | 12.6 | 17.0 | 10.2 |
| $C_4$ | 14.6 | 13.2 | 7.4 |
| $C_5+$ | 58 | 54 | 60 |
| % Aromatics in | | | |
| $C_6$ | 12.3 | 19 | 16.7 |
| $C_7$ | 25.4 | 36 | 33.3 |
| $C_8$ | 28.2 | 34 | 31.9 |
| $C_9$ | 28.8 | | 29.3 |
| $C_{10}$ | | | 22.0 |
| $C_{11}$ | | | 11.2 |

As is seen from the data, the hydrocarbon selectivities again show good agreement.

EXAMPLE 9

The following runs were made in the apparatus described in Example 5 using the same 10:1 Fe/Tl described in Example 5, the 20:1 Fe/Tl catalyst described in Example 6, and a 100 Fe:4K catalyst, prepared by the technique described in Example 2, except that sufficient $K_2CO_3$ was used to achieve a 4 weight percent potassium loading. (Note: the pretreatment procedure given to Catalyst C was the same as for the other catalysts, for comparative purposes, and did not include the more vigorous high temperature sintering step which would normally be administered). Also tested was a commercial ammonia synthesis catalyst, Catalyst D. The runs were made at 0.9 MPa, with a 1:1 by volume $CO/H_2$ feed. The particular temperatures and space velocities (GHSV) used are given in the following Tables. Table X lists the percent CO conversion, percent selectivity to hydrocarbons, percent methane produced, percent $C_1-C_5$ hydrocarbons produced and percent $C_6-C_{11}$ liquid hydrocarbons produced. Table XI lists percent of CO which is converted to: $C_{12}-C_{23}$ hydrocarbons, wax ($C_{23}+$), aromatics, and alpha-olefins.

Catalyst A is 100 Fe:10 Tl;
Catalyst B is 100 Fe:20 Tl;
Catalyst C is 100 Fe:4K; and
Catalyst D is a commercial $NH_3$ synthesis catalyst.

TABLE X

Results of Integral Reactor Studies of CO Hydrogenation over Iron Catalysts: Conversion of Selectivity to Lighter Products: P = 0.9 MPa, Feed = 1.0 CO/1.0 $H_2$

| Run | Catalyst | Temp., °C. | GHSV | % CO Conv | % Selec | % $CH_4$ | % $C_1-C_5$ | % $C_6-C_{11}$ |
| --- | --- | --- | --- | --- | --- | --- | --- | --- |
| 1 | A | 270 | 300 | 78.6 | 64.6 | 4.5 | 35.0 | 46.2 |
| 2 | A | 270 | 300 | 46.8 | 69.9 | 3.4 | 30.4 | 44.8 |
| 3 | A | 300 | 300 | 62.5 | 61.9 | 3.5 | 39.0 | 44.6 |
| 4 | A | 300 | 300 | 78.1 | 60.4 | 4.5 | 37.3 | 46.4 |
| 5 | A | 325 | 300 | 95.5 | 58.8 | 7.8 | 42.0 | 45.0 |
| 6 | A | 350 | 300 | 96.7 | 60.9 | 10.1 | 38.4 | 45.3 |
| 7 | A | 350 | 300 | 63.6 | 62.5 | 13.0 | 44.7 | 45.4 |
| 8 | A | 375 | 300 | 55.4 | 56.2 | 21.9 | 52.8 | 38.4 |
| 9 | A | 400 | 300 | 81.6 | 54.9 | 21.0 | 48.4 | 39.1 |
| 1 | B | 270 | 150 | 81.9 | 63.4 | 5.2 | 43.3 | 47.8 |
| 2 | B | 270 | 150 | 88.1 | 65.4 | 5.8 | 38.8 | 45.5 |
| 3 | B | 270 | 375 | 50.6 | 66.7 | 6.7 | 45.2 | 42.2 |
| 4 | B | 300 | 150 | 97.7 | 65.6 | 5.7 | 44.5 | 45.6 |
| 5 | B | 325 | 200 | 97.2 | 64.7 | 14.2 | 62.5 | 31.6 |
| 6 | B | 350 | 300 | 45.0 | 59.6 | 16.6 | 46.6 | 39.0 |
| 7 | B | 375 | 300 | 33.6 | 62.6 | 23.6 | 55.2 | 35.0 |
| 1 | C | 270 | 300 | 68.9 | | 3.0 | | |
| 2 | C | 300 | 300 | 51.1 | 60.5 | 6.8 | 21.2 | 27.5 |
| 3 | C | 325 | 300 | 89.5 | 54.8 | 11.6 | 29.2 | 30.0 |
| 4 | C | 350 | 300 | 55.5 | 66.0 | 11.1 | 31.8 | 32.5 |

TABLE X-continued

Results of Integral Reactor Studies of CO Hydrogenation over Iron Catalysts: Conversion of Selectivity to Lighter Products: P = 0.9 MPa, Feed = 1.0 CO/1.0 $H_2$

| Run | Catalyst | Temp., °C. | GHSV | % CO Conv | % Selec | % $CH_4$ | % $C_1$-$C_5$ | % $C_6$-$C_{11}$ |
|---|---|---|---|---|---|---|---|---|
| 5 | C | 375 | 300 | 33.6 | 64.1 | 10.6 | 38.2 | 47.2 |
| 1 | D | 350 | 300 | 97.1 | 69.5 | 3.3 | 42.2 | 42.3 |

TABLE XI

Results of Integral Reactor Studies of CO Hydrogenation over Iron Catalysts: Selectivity to Heavier Products, Aromatics and α-Olefins

| | | | | % CO Converted to Listed Products | | | |
|---|---|---|---|---|---|---|---|
| Run | Cat-alyst | Temp., °C. | GHSV | $C_{12}$-$C_{23}$ | $C_{23}^+$ | Aro-matics | α-Olefins |
| 1 | A | 270 | 300 | 18.1 | 0.7 | 3.32 | 22.52 |
| 2 | A | 270 | 300 | 23.8 | 1.0 | 2.92 | 22.31 |
| 3 | A | 300 | 300 | 15.5 | 0.9 | 3.87 | 21.31 |
| 4 | A | 300 | 300 | 15.2 | 1.1 | 3.36 | 23.46 |
| 5 | A | 325 | 300 | 12.8 | 0.2 | 6.83 | 18.38 |
| 6 | A | 350 | 300 | 16.0 | 0.3 | 12.70 | 14.93 |
| 7 | A | 350 | 300 | 9.7 | 0.2 | 14.02 | 9.66 |
| 8 | A | 375 | 300 | 7.5 | 1.3 | 14.21 | 4.16 |
| 9 | A | 400 | 300 | 12.4 | 0.1 | 20.44 | 4.44 |
| 1 | B | 270 | 150 | 8.8 | 0.1 | 2.65 | 23.88 |
| 2 | B | 270 | 150 | 14.1 | 1.6 | 4.01 | 16.39 |
| 3 | B | 270 | 300 | 9.8 | 2.8 | 2.73 | 15.17 |
| 4 | B | 300 | 150 | 9.8 | 0.1 | 2.17 | 22.53 |
| 5 | B | 325 | 150 | 5.8 | 0.1 | 3.2 | 14.61 |
| 6 | B | 350 | 300 | 13.6 | 0.8 | 10.3 | 10.0 |
| 7 | B | 375 | 300 | 10.0 | −0.2 | 11.2 | 10.7 |
| **1 | C | 270 | 300 | | | | |
| 2 | C | 300 | 300 | 37.5 | 13.8 | 3.36 | 23.46 |
| 3 | C | 325 | 300 | 31.2 | 9.6 | 4.6 | 13.6 |
| 4 | C | 350 | 300 | 24.9 | 10.8 | 6.57 | 16.69 |
| 5 | C | 375 | 300 | 13.5 | 1.1 | 13.26 | 6.14 |
| 1 | D | 350 | 300 | 14.8 | 0.7 | 8.65 | 11.43 |

**Wax buildup

Key results are given in Tables X and XI. Percentage conversion of CO and the percentage selectivity of this conversion to hydrocarbons are given in the 5th and 6th columns of Table X, respectively. In general, it has been found that a potassium-promoted iron catalyst loses substantial hydrocarbon synthesis activity within relatively short periods of time as contrasted to thallium-promoted iron catalyst, which maintains a higher hydrocarbon synthesis activity for longer periods of time. Selectivities of CO conversion to hydrocarbons ranged consistently between 54 to 70 percent for all catalysts. Methane selectivity (weight percentage of $CH_4$ in hydrocarbon products) appears to correlate with temperature, ranging from 4 percent at 270° C. to 22 percent at 375° C. This correlation was statistically significant for all three catalysts ($p < 0.05$).

Differences between Fe/Tl and Fe/K catalyst in $C_1$-$C_5$, $C_6$-$C_{11}$, $C_{11}$-$C_{23}$ and $C_{23+}$ selectivities clearly exist. The Fe/Tl catalyst tends to make ligher products than Fe/K (columns 8 and 9 in Table X and columns 5 and 6 in Table XI). Virtually no wax is made by Fe/Tl, whereas 10 percent of the hydrocarbons (by weight) made by Fe/K are in the $C_{23+}$ range.

The aromatics yield, as a percentage of total hydrocarbons produced, is seen to increase with temperature for all three catalysts. For 100 Fe:10 Tl, this correlation is significant ($p < 0.01$), but is not quite significant for 100 Fe:20 Tl or 100 Fe:4K. At 300° to 325° C., the latter two catalysts appear similar in this respect, but at 350° C., 100 Fe:10 Tl produces about twice as much aromatics as does 100 Fe:4K. Above 350° C., the Fe/K catalyst plugged and lost activity, probably due to coke formation. On the other hand, wax accumulated on this particular catalyst at temperatures below 325° K., greatly complicating the product assay. Thus, comparative experiments outside the temperature range of 325° to 350° C. are difficult to perform with Fe/K.

There is a rather striking statistical negative correlation between the percentages of aromatics and α-olefins in the $C_6$-$C_{11}$ cut indicating an inverse relationship. Because α-olefins are thought to be primary products of Fischer-Tropsch synthesis, this suggests that olefins are converted to aromatics and that the rate of this conversion increases with temperature.

From the data, Fe/Tl catalyst appears to make a lighter and narrower product distribution than Fe/K where the two catalysts are pretreated under substantially the same conditions not involving sintering. In addition, Fe/Tl has good total selectivity (percentage of converted CO that goes to hydrocarbons) and low selectivity to methane production. The aromatics yield of Fe/Tl is comparable to that obtained from Fe/K except at >350° C., where it is difficult to obtain data on Fe/K due to coking and deactivation, as described above. About 10 percent of the hydrocarbons (by weight) produced by Fe/Tl at 350° C. are aromatics. In the $C_6$-$C_{11}$ cut range, this corresponds to 25 percent of the cut. Thus, the $C_6$-$C_{11}$ cut represents an attractive feedstock for an aromatics separations process.

EXAMPLE 10

To show that the catalyst must be pretreated to yield metallic thallium and reduced and carbided iron, the pretreatment was only partially completed, yielding metallic thallium and a mixture of oxidized, reduced and carbided iron. It is necessary to operate the process at reduced temperatures, below about 230° C., to ensure that iron in the catalyst remains in this state of multiple valencies. Under these conditions, 200° C., 8.2 atm to 16.3 atm, and 300 v/v/hr, essentially no aromatic hydrocarbons were produced and a large fraction of the products were in the form of oxygenated hydrocarbons and, especially, as alcohols. This form of the catalyst is the subject of a copending patent application. Following operation of the process at these lower temperatures, the process conditions were changed to complete the reduction and carbide formation, namely the temperature was increased to 270° C., the pressure was maintained at 8.2 atm and the space velocity was maintained at 300 v/v/hr. At these conditions, the alcohol yield decreased, as shown in Table XII. A corresponding increase in the yield of non-oxygenated hydrocarbons, especially alpha olefins and paraffins, was observed as the alcohol yield decreased. Concurrently, the catalyst became totally reduced and carbided. The temperature was then again reduced to 175° to 200° C., with the other conditions remaining constant, that is, the pressure was 8.2 atm and the space velocity was 300 v/v/hr. At these conditions, the catalyst was not very active, as indicated by CO conversions in the range of 10 to 15 percent. This shows that the process for producing liquid hydrocarbons and aromatic hydrocarbons in the $C_6$-$C_{11}$ range is preferably carried out at higher temperatures in the range of 250° to 550° C., preferably 270° to 400° C., and that the catalyst should be fully pretreated to yield a working catalyst consisting substantially of metallic thallium and reduced and carbided iron.

TABLE XII

|  | Time (hours) | | | |
| --- | --- | --- | --- | --- |
|  | 23 | 71 | 95 | 167 |
| % CO Conv. | 65 | 64 | 65 | 68 |
| $CO_2$ Sel.[a] | 31 | 32 | 30 | 32 |
| HC Sel.[b] | 69 | 68 | 70 | 68 |
| $C_1$-$C_{19}$ ROH[c] | 17.9 | 8.4 | 8.1 | 7.0 |
| $C_6$-$C_{12}$ ROH[d] | 3.8 | 2.0 | 2.2 | 1.9 |
| % $C_6$-$C_{12}$ ROH[e] | 12.6 | 5.4 | 5.3 | 5.0 |
| % Methane[f] | 4.3 | 4.7 | 4.5 | 4.8 |

[a]Percent CO converted to $CO_2$.
[b]Percent CO converted to total hydrocarbons including alcohols.
[c]$C_1$-$C_{19}$ alcohols produced as weight percent of total produced hydrocarbons.
[d]$C_6$-$C_{12}$ alcohols as weight percent of total produced hydrocarbons.
[e]Weight percent $C_6$-$C_{12}$ alcohols of $C_6$-$C_{12}$ produced hydrocarbons.
[f]Percent methane produced as weight percent of total produced hydrocarbons.

What is claimed is:

1. A process for producing liquid hydrocarbons, including those in the $C_6$-$C_{11}$ hydrocarbon range, comprising the steps of:
   (a) first depositing thallium on the surface of a supported or unsupported iron catalyst wherein the weight ratio of iron-thallium, taken as the free metals, is from about 100:1 to 1:100, and wherein said iron compounds contain iron value substantially in the trivalent state;
   (b) contacting said iron-thallium catalyst with a mixture of CO and $H_2$ in a volume ratio of about 1:4 to 4:1, respectively, at a temperature ranging from 270° to 550° C., a pressure ranging from 0.1, to 10 MPa and a space velocity ranging from 10 to 10,000 v/v/hr., or equivalent conditions, for a sufficient time to substantially convert said thallium compounds to metallic thallium and said iron compounds to reduced and carbided iron; and
   (c) continuing said contacting as described in step (b) at a pressure above 0.1 MPa, a temperature ranging from 230° to 550° C., to produce liquid hydrocarbons comprising about 40 weight percent and greater $C_6$-$C_{11}$ liquid hydrocarbons and below about 5 weight percent $C_{23+}$ hydrocarbons.

2. The process of claim 1 wherein said product $C_6$-$C_{11}$ hydrocarbons comprise at least about 5 weight percent of $C_6$-$C_{11}$ aromatic hydrocarbons.

3. The process of claim 2 wherein said temperature is 350° C. and above in step (b) and said $C_6$-$C_{11}$ product hydrocarbons comprise about 10 weight percent $C_6$-$C_{11}$ aromatic hydrocarbons.

4. The process of claim 1 wherein said temperature is 270° to 350° C. in step (b) and said liquid product hydrocarbons comprise about 20 weight percent and greater $C_6$-$C_{11}$ alpha olefins.

5. The process of claim 1 wherein said $C_{23+}$ hydrocarbons are present in less than three weight percent.

6. The process of claim 1 wherein the weight ratio of iron-thallium, taken as the free metals, is from about 100:1 to about 35:65.

7. The process of claim 6 wherein said weight ratio of iron-thallium, taken as the free metals, is from about 100:10 to 80:20.

8. The process of claim 1 wherein said catalyst is supported on $Al_2O_3$, alkali-doped $Al_2O_3$, $SiO_2$, $TiO_2$, MgO, $MgCO_3$, silicon carbide, zirconia, or mixtures thereof.

9. The process of claim 1 wherein said compounds of iron and thallium are selected from their oxides, hydroxides, carbonates, sulfates, carbides, halides, nitrates, or mixtures thereof.

10. The process of claim 9 wherein said iron compound is iron oxide.

11. The process of claim 9 wherein said thallium compound is thallium oxide, thallium chloride, thallium fluoride, thallium nitrate, or mixtures thereof.

12. The process of claim 1 wherein said catalyst composition further contains a promoter agent.

13. The process of claim 12 wherein said promoter agent is selected from cobalt, zinc, chromium, manganese, barium, as their salts or oxides, ammonium fluoride, potassium carbonate, or mixtures thereof.

14. The process of claim 1 wherein the mixture of CO and $H_2$ in step (b) is in a volume ratio of about 2:1 to 1:2, respectively.

15. The process of claim 1 wherein said temperature in step (b) is about 270° to 400° C.

16. The process of claim 1 wherein said pressure in step (b) is about 0.5 to 1.5 MPa.

17. The process of claim 1 wherein said catalyst is in the form of a fixed bed.

18. The process of claim 1 wherein said catalyst is in the form of a fluid bed.

19. The process of claim 1 wherein said first contacting in step (a) is carried out at 270° C., 0.1 MPa pressure, a space velocity of 300 to 500 v/v/hr. using a mixture of CO and $H_2$ at a volume ratio of 1:1, respectively.

20. The process of claim 1 wherein said velocity in step (b) is in the range of 100 to 2500 v/v/hr.

21. A process for producing liquid hydrocarbons, including those in the $C_6$-$C_{11}$ hydrocarbon range, comprising the steps of:
   (a) first depositing thallium nitrate or oxide on the surface of a supported iron catalyst to form an iron-thallium catalyst the weight ratio or iron:thallium, taken as the free metals in the composition, being from about 100:1 to 65:35, said support being aluminum oxide, magnesium oxide or mixtures thereof;
   (b) contacting said iron thallium catalyst with a mixture of CO and $H_2$ at a volume ratio of 1:1 at about 270° C., at 0.1 MPa pressure, a space velocity of 300 to 500 v/v/hr, for a sufficient time to substantially convert said thallium compound to metallic thallium and said iron oxide to reduced and carbided iron; and
   (c) continuing said contacting as described in step (b) at a temperature ranging from 270° to 350° C. a pressure ranging from 0.5 to 1.5 MPa, and a space velocity ranging from 150 to 1500 v/v/hr, to produce hydrocarbons comprising $C_6$-$C_{11}$ liquid hydrocarbons comprised of about 20 weight percent alpha olefin hydrocarbons and less than about one weight percent $C_{23+}$ hydrocarbon waxes.

22. A process for producing liquid hydrocarbons, including those in the $C_6$-$C_{11}$ hydrocarbon range, comprising the steps of:

(a) first depositing thallium nitrate or oxide on the surface of a supported iron oxide catalyst to form an iron thallium catalyst, the weight ratio of iron:-thallium, taken as the free metals in the composition, being from about 100:1 to 65:35, said support being aluminum oxide, magnesium oxide, or mixtures thereof;

(b) contacting said iron thallium catalyst with a mixture of CO and $H_2$ at a volume ratio of about 1:1 at about 270° C., at 0.1 MPa pressure, a space velocity of 300 to 500 v/v/hr, for a sufficient time to substantially convert said thallium compounds to metallic thallium and said iron oxide to reduced and carbided iron; and (c) continuing said contacting described in step (b) at a temperature ranging from 350° to 550° C., a pressure ranging from 0.5 to 1.5 MPa, and a space velocity ranging from 150 to 1500 v/v/hr, to produce hydrocarbons comprising $C_6$–$C_{11}$ liquid hydrocarbons comprised of at least about 25 weight percent $C_6$–$C_{11}$ aromatic hydrocarbons and less than about one weight percent $C_{23+}$ hydrocarbon waxes.

* * * * *